(12) United States Patent
Ideker et al.

(10) Patent No.: US 7,020,530 B1
(45) Date of Patent: Mar. 28, 2006

(54) METHOD AND APPARATUS FOR PASSIVE CARDIAC STIMULATION

(75) Inventors: Raymond E. Ideker, Birmingham, AL (US); Steven D. Girouard, Woodbury, MN (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 10/019,873

(22) PCT Filed: Mar. 30, 2000

(86) PCT No.: PCT/US00/08695

§ 371 (c)(1),
(2), (4) Date: Aug. 26, 2002

(87) PCT Pub. No.: WO00/57950

PCT Pub. Date: Oct. 5, 2000

Related U.S. Application Data

(60) Provisional application No. 60/126,867, filed on Mar. 30, 1999.

(51) Int. Cl.
*A61N 1/362* (2006.01)
*A61N 1/39* (2006.01)

(52) U.S. Cl. ............................. 607/122; 607/5; 607/9
(58) Field of Classification Search ........ 607/122–128, 607/5, 9; 600/373–381
See application file for complete search history.

(56) References Cited

U.S. PATENT DOCUMENTS 5,968,086 A   10/1999   Bonner et al. .............. 607/122

*Primary Examiner*—Jeffrey R. Jastrzab
(74) *Attorney, Agent, or Firm*—Gifford, Krass, Groh, Sprinkle, Anderson, & Citkowski, P.C.

(57) ABSTRACT

This invention is a passive conductor assembly for use with an implanted device having an intra-cavitarily or transvenously disposed electrode. The assembly can include electrical components in electrical communication therewith which provide for the manipulation, and/or modification of the electrical stimulus or waveform generated by the implanted stimulus generator, which can be designed, for example, to selectively stimulate only neural tissue, not cardiac tissue or vice versa through the same passive conductor assembly.

29 Claims, 1 Drawing Sheet

POTENTIAL DISTRIBUTION

METHOD AND APPARATUS FOR PASSIVE CARDIAC STIMULATION

This application claims the benefit of Provisional Application No. 60/126,867, filed Mar. 30, 1999.

GRANT REFERENCE

The subject invention was made with government support under grants from the National Institutes of Health, Grant Nos. HL-42760 and HL-28429. The government has certain rights in the invention.

The subject invention was also made with support from Guidant Corporation, 4100 Hamline Avenue North, St. Paul, Minn. 55112-5798. Guidant Corporation has certain rights in the invention.

TECHNICAL FIELD

The subject invention relates to a method and apparatus for cardiac stimulation. In particular, the subject invention provides a passive conductor for use in combination with an implanted stimulating device for passively stimulating remote regions of the heart and a method of using same.

BACKGROUND OF THE INVENTION

By way of background, the application of electrical current to the heart through electrodes either applied directly to the chest or through an implanted device is well known in the art. Typical implanted devices include defibrillators and/or pacemakers. These types of devices are usually surgically implanted into a subject and an intracavitary electrode is placed within or adjacent to the heart, typically transvenously.

While these implanted stimulating devices competently carry out their design task, there are many instances in which it would be desirable to electrically stimulate a portion of the heart that is either difficult to reach with a transvenously disposed electrode or which has been previously connected to an implanted electrode. For example, locations such as, but not limited to, the left ventricular apex, the anterior-basal left ventricular free wall, and the left atrium near the pulmonary veins. It may be necessary and advantageous to electrically stimulate the heart from these regions for reasons including multi-site pacing for congestive heart failure, single or multi-site pacing to prevent a ventricular or atrial tachyrhythmia, single or multi-site pacing very soon after the onset of an arrhythmia to halt the arrhythmia before it degenerates into ventricular or atrial fibrillation requiring a defibrillation shock, and multi-site electrodes for delivery of shocks with a lower defibrillation threshold than shocks delivered only through transvenous electrodes.

While electrodes on catheters inserted into veins of the heart by way of the coronary sinus can be placed in many cardiac locations, there are a number of spots or locations to which they cannot reach or be placed. Electrodes can be placed in almost any desired epicardial location during open-heart surgery. However, such surgery is expensive and is associated with both mortality and morbidity of the subject. With the advent of thoracoscopic surgery, it is now possible to implant such electrodes in the pericardial space by a much more minor procedure that requires only one or two small incisions for the insertion of a thoracoscopic device. However, this type of procedure is still complicated by the fact that the electrodes still must be connected to wires that are tunneled through the body to the pacemaker or defibrillator.

It has been recognized that the heart is under profound control of the autonomic nervous system. There are many instances when electrical stimulation of the neural input to the heart could be beneficial for the alteration of cardiac electrophysiologic status. The difficulty in implementing neural stimulation of the heart has been in the development of an apparatus for the direct stimulation or inhibition of cardiac sympathetic and parasympathetic nerves.

Accordingly, it would be advantageous and desirable to have an apparatus and method for stimulating portions of the heart which are difficult or impossible to reach or stimulate with a transvenous electrode but which are accessible utilizing the less invasive thoracoscopic surgical technique and which is able to stimulate the remote regions of the heart without the necessity for tunneling wires through a body of the subject and connection to a pacemaker or defibrillator for a source of electrical stimuli.

Furthermore, it would also be advantageous and desirable to have a method and apparatus which allows for the selective stimulation of the heart.

SUMMARY OF THE INVENTION

A passive conductor assembly for use with an implanted stimulating device having an intracavitarily or transvenously disposed electrode is disclosed. The passive conductor assembly for use in combination with the implanted stimulus generator having an intracavitarily or intravenously disposed electrode includes at least one conductive element having a first end and a second end, and/or other contact sites for contacting a desired or selected portion of a heart of a subject to be stimulated. The passive conductor assembly is disposed in proximity to the intracavitarily or transvenous electrode which is connected to the implanted stimulus generator such as a pacemaker or defibrillator. Upon discharge of an electrical stimulus or waveform from the implanted stimulus generator, the stimulus is conducted through the myocardial tissue to the conductor where it is passively conducted to a region of the heart in contact with an end or other contact sites of the conductive element of the passive conductor assembly which have been selected for cardiac stimulation.

The passive conductor assembly can include electrical components disposed in electrical communication therewith to provide for the manipulation and/or modification of the electrical stimulus or waveform generated by the implanted stimulus generator which can be designed, for example, to selectively stimulate only neural tissue and not cardiac tissue or vice versa through the same passive conductor assembly.

BRIEF DESCRIPTION OF THE DRAWINGS

The following detailed description is best understood with reference to the following drawings in which.

Figure 1:
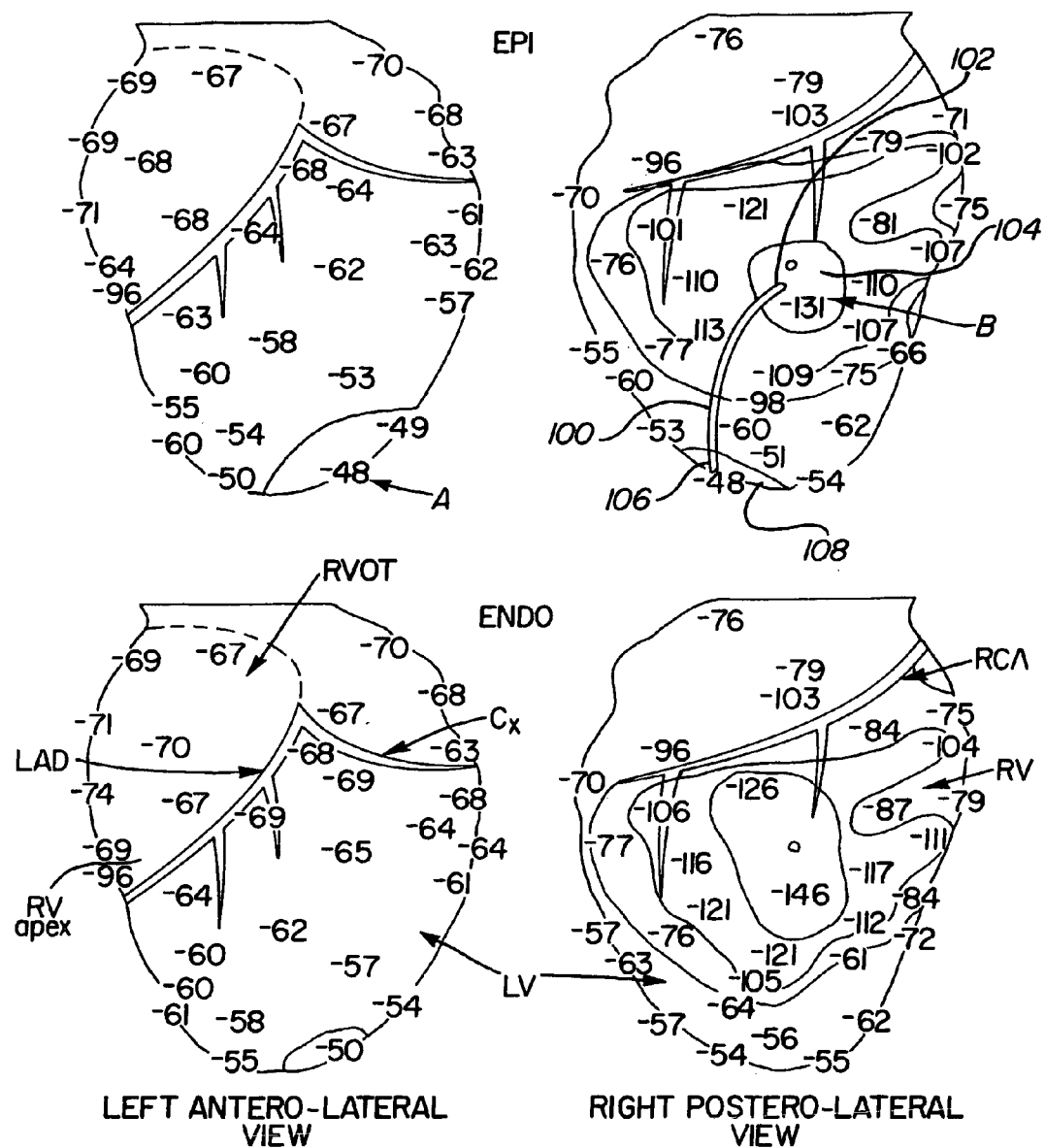
FIG. 1 illustrates the potential field from a 500-V 6 ms unsuccessful defibrillation shock. The top two panels represent the subepicardial potentials, and the bottom two panels represent the subendocardial potentials. All panels show the potentials superimposed on the epicardial surface of the heart. The two panels on the left represent the left antero-lateral view of the heart, whereas the two panels on the right represent the right postero-lateral view of the heart. Numbers denote the location of the recording electrodes and the potential in volts recorded at each site. Isopotential lines are separated by 25V. Solid circles represent locations where good recordings were not obtained. The dashed line indicates the upper border of the right ventricular outflow tract.

LV=left ventricle; RV=right ventricle; RVOT=right ventricular outflow tract; LAD=left anterior descending coronary artery; RCA=right coronary artery; Cx=circumflex coronary artery.

DETAILED DESCRIPTION OF THE INVENTION

The present invention provides for a passive conductor assembly used in combination with an implanted cardiac stimulation device or generator such as a pacemaker or a defibrillator having an intracavitarily or intravenously disposed electrode. The passive conductor assembly can be placed by surgery or thoracoscopy to electrically stimulate the heart of a subject which does not require the running or tunneling of wires from the passive conductor assembly to the implanted stimulus generator. That is, the passive conductor assembly can be completely self-contained or disposed completely within the pericardial space of the heart and used in conjunction with a defibrillator or a pacemaker connected to leads or electrodes that are inserted into the heart.

The passive conductor assembly includes at least one conductive element having a first end, a second end, and/or other contact sites for contacting a portion of the heart of the subject. The conductive element is preferably comprised of a low-resistance material and can have any suitable length but typically ranges from approximately 1 cm to approximately 12 cm. The conductive element can be made of any conductive material but is preferably constructed of a metallic material in the form of wire or strips that are placed in the pericardial space and contact the heart. Additionally, the conductive element can be constructed of a composite ribbon of conductive material. The conductive elements can be exposed to the heart along their entire length forming a single electrode, however, in a preferred embodiment, the conductive element is insulated along most of its length except at the two ends or other intermediate sites which form the electrodes or contact sites.

The insulator can comprise any suitable electrically insulative material that is also biocompatible. In a further embodiment, the insulation can be removed at one or more additional locations along the conductive elements to stimulate additional sites of the heart.

The ends of the conductive element should be placed at the points on the heart at which the electrical stimulus or waveform delivered by the pacemaker or the defibrillator, through their own transvenous electrode, creates a potential differential on the surface of the heart to facilitate the flow of the electrical stimulus. That is, if the two ends of the conductive element are placed at sites that have approximately the same electrical potential, little or no current will flow therethrough.

The exposed portions (ends and/or regions therebetween) of the conductive element in the contact with the heart can vary in size depending on the current density and the potential gradient in the immediately adjacent tissue. Typically, the contact portion of the conductive element can range from approximately 0.2 mm to 4 cm.

In order to modify the electrical stimulus or waveform received from the implanted stimulus generator, electrical components can be disposed in electrical communication with or along the conductive element. These electrical components can include, for example, diodes, devices capable of storing energy such as capacitors, microprocessors, resistors, and the like. The electrical components can also be used in combinations such that the passive conductor can act as a low-pass or high-pass filter to modify the input stimulus or waveform from the implanted stimulus generator. In another embodiment, a diode could be placed along the conductive element such that the stimulus or electrical current could only flow in one direction along the conductive element during the stimulation. This embodiment has several advantages, for example, it becomes possible to pace from some sites in the heart but not others by controlling which polarity of stimulus was generated by the implanted stimulus generator through its electrode(s). If two or more conductors are utilized, then the diode could be oriented in one direction for some of the electrodes and oriented in the opposite direction for other of the electrodes so that the first set of electrodes would pass current with one polarity while the other set would pass current of the other polarity. An additional set of conductors could contain no diode such that they would pass current with either polarity. The use of electrical components disposed along the conductive element increases the flexibility of stimulating of myocardium in different combinations and in different sequences.

Diodes may also be useful for delivering defibrillation and cardioversion shocks. A concern when delivering a shock through two or more electrodes that are of the same polarity and the same or nearly same strength, is that a region of little current flow and potential gradient will be created oil the heart at the point somewhere between the common polarity electrodes. Creation of this low field region could significantly increase the defibrillation and cardioversion thresholds. Currently, most defibrillation shocks are biphasic with a second phase opposite in polarity to the first phase. The presence of the diode in one or more of the conductive elements would allow current to flow during one phase but not the other phase of the biphasic waveform. Therefore, the region of low field strength would only be present during one of the two phases of the shock so that the area could receive a stronger defibrillating field strength during the other phase.

In a further embodiment designed to avoid the region of low field strength throughout all phases of the shock, a capacitor is utilized instead of a diode along the length of the conductive element. The capacitor would allow current to flow during the early portion of the shock pulse thereby creating the low field strength region, but would not allow much current to flow later during the pulse, at which time the low field strength region would no longer be of the same strength and location. Towards the end of the shock pulse and after the shock pulse, the capacitor would discharge, creating a biphasic shock effect in some portions of the heart. If the shock pulse delivered from the defibrillator is, itself, biphasic, the second phase could be delivered either immediately after the first phase or after an interval of up to 5 ms or more since it has been shown that such a separation does not significantly decrease the beneficial effects of a biphasic pulse on defibrillation. Cooper et al. Pace, 16:471–482 (1993). Thus, with a short interval between the two phases of the shock, the capacitor would discharge during the second phase either partially or entirely followed by charging in the opposite polarity toward the end of the second phase. This interaction would change the ratio of the currents passing through the passive conductor assembly and through the active intravascular defibrillation electrodes throughout the pulses. Accordingly, the size and location of the low field regions should change throughout the pulses instead being fixed in one region. The movement of this low field strength region should have a beneficial effect on the defibrillation threshold.

Alternatively, the two active phases of the shock could be separated by up to 5 or more ms so that the capacitor will largely discharge between the two phases and following the second active phase.

Biphasic pulses are frequently used for pacing to prevent electrolysis and the plating or the unplating of the pacing electrodes that can occur with a single polarity pulse. Disposing a capacitor along the length of the conductor would generate a biphasic pacing pulse since it allows only a zero net charge to pass through the conductor after it has been discharged.

Other electronic components used in combination with the passive conductor assembly could be useful. These components could be powered by the current that passes through the conductive element when a stimulus is delivered through the active intravascular electrodes of the pacemaker or defibrillator. Electronic components could store the charge to power the other components disposed along the conductive element for some period of time following pulses delivered by the pacemaker or the defibrillator. The pulses to charge these electronic components could either be delivered whenever needed to treat or prevent arrhythmias or the pacemaker or defibrillator could deliver a small stimulus at specific time intervals for the sole purpose of charging the components disposed along the conductive element. This small stimulus could be of a frequency that does not stimulate the myocardium.

The electronic components that are powered along the conductive elements could perform several functions, for example, sensing activations at the ends or contacts on the conductive element. Pacing stimuli or shocks at these points along the conductive element could be time-based oil the recorded activations from these electrodes. The timing algorithms could be performed by the electronic components disposed along the conductive element. Alternatively, the power in the conductive element could be used to pass a signal to the pacemaker or the defibrillator or its recording electrodes so that the software within the pacemaker or the defibrillator could control and integrate the responses of all of the passive conductors. Communication signals between the components disposed along the conductive element of the passive conductor and the pacemaker or the defibrillator could be by any modality including electrical or optical. If electrical, the frequency and strength of the signal could be such that the signal does not cause stimulation of the heart.

The passive conductor assembly is preferably oriented so that, during an electrical pulse delivered by the separated implanted stimulus generator, a potential difference is generated between the ends or other exposed regions (electrodes) of the conductive element disposed in the pericardial space. Typically, at least one of the electrodes will be placed on the epicardium overlying one of the implanted stimulus generator leads or electrodes located within the cavities of the heart or veins. However, other orientations may also be useful. For example, as reported in a study by Callihan et al., (*JACC,* 1995; 25:1373–1379), it was found that a passive patch electrode located distant from the defibrillation electrodes of an implanted cardioverter/defibrillator would transfer most of the potential gradient that would normally be present beneath this electrode to concentrate it at the edges of the electrode. For a small electrical stimulus, this effect may make it possible to pace from the edge of the electrode with an electrical stimulus that would not be strong enough to pace this region in the absence of the passive conductor.

As stated above, the present invention provides a method and device for the stimulation or the inhibition of neural inputs to the heart with the purpose of preventing atrial or ventricular arrhythmias, terminating atrial or ventricular arrhythmias, assisting in atrial or ventricular defibrillation, control of heart-rate variability, or the improvement of cardiac function. By adding the passive electrical components to the passive conductive element and modulating the frequency of stimulation of the intracavitary electrode therewith, the present invention allows for selective stimulation and/or inhibition of neural tissue and not cardiac tissue or vice versa through the same passive conductor assembly.

The device for the extra-cardiac stimulation or inhibition of neural inputs to the heart is similar if not identical to the device described immediately above. The uninsulated portions (electrodes) of at least one conductive element are disposed in contact with the heart and/or other tissues such as neural tissue, fat pads containing post-ganglionic neural fibers, cardiac veins adjacent to neural fibers, or other electrically excitable tissues such as the stellate ganglia and the vagus. The conductive element can also run circumferentially along the atrial-ventricular groove of the heart such that the sympathetic and the parasympathetic innervation, running parallel to cardiac vasculature, can be directly stimulated or inhibited. Typically, the electrical stimulation or inhibition will be achieved with the application of stimuli from approximately 1 to 20 mA at a frequency of approximately 1 to 50 Hz. For neural stimulation, the stimulus could have a pulse width from approximately 10–250 μsec, a current of approximately 1–20 mA, and a frequency of approximately 1–50 Hz. For cardiac stimulation, the stimulus could have a pulse width from approximately 0.5–2 msec, a current of approximately 1–20 mA and a frequency of approximately 1–5 Hz.

The conductive element should be oriented such that when an electrical stimulus or pulse is delivered from the implanted stimulus generator, an electrical potential difference will be created on the epicardial surface between the two or more exposed electrodes on the conductive element. As a result of this potential difference, current will be induced to flow in the conductive element. To achieve a sufficient potential difference in the passive conductor assembly, at least one conductive element should be placed in close proximity to the cardiac tissue overlying either an intracavitary electrode in an atrial or ventricular chamber, cardiac vein, or other location in or near the heart.

Alternatively, the passive conductor assembly having at least one conductive element may be placed in the pericardial space, an extra-pericardial space, or in other extra-cardiac locations. The passive conductor assembly can be placed during surgery that exposes these locations directly or may be placed using minimally invasive techniques such as thoracoscopic surgery, or transvenously through an introducing catheter. Additionally, passive conductor assemblies for both neural stimulation/inhibition can be combined with passive conductor assemblies for directly exciting cardiac tissue.

The largest effect utilizing the passive conductor assembly of the present invention is generally seen when one end of the conductive element is placed directly on the epicardium over the intravenous electrode of the stimulus generating device. However, this does not have to be the case. In order to refine the placement of the passive conductor assembly, it may be helpful to map the regions of the heart that depolarize and hyperpolarize in the absence of the passive conductor assembly during a stimulus passed through the intravenous electrode. The implanted stimulus generator should cause hyperpolarization at one end and depolarization at the other. Accordingly, it should be possible to place the passive conductor assembly in a region that is normally undergoing depolarization induced by the stimulus. These two effects should be additive so that the amount of stimulus needed to directly stimulate the particular region or area of the heart should be lower than when the end of the conductive element that causes depolarization is placed in a region that is undergoing hyperpolarization caused by the electrical stimulus through the transvenously disposed electrodes. It is also possible that a similar beneficial effect might be seen if the end of the conductive element that causes hyperpolarization is placed in a region that is already undergoing hyperpolarization during the electrical stimulus.

As is stated above, more than one passive conductor assembly can be used in the same subject. For example, arrhythmias may be prevented by simultaneously stimulating from several sites on the heart. Two, three, or even more of the passive conductor assemblies could be placed in the pericardial space to pace from all of the sites. Even though the stimulus strength will be larger than if it was directly paced at each of the sites with electrodes connected directly to the implanted stimulus generator, the strength of the electrical stimulus should still be smaller than that required to directly activate all of these regions by a stimulus from the transvenous electrodes in the absence of the passive conductors of the present invention.

The passive conductor assembly of the present invention can be used for prevention and treatment of atrial-arrhythmias, ventricular arrhythmias, as well as for the control of cardiac performance through control of heart rate and atrial and ventricular refractory periods. Additionally, the passive conductor assembly can be used for the control of heart rate through stimulation of neural inputs to the sino-atrial and atrial-ventricular nodes of the heart.

Use of the passive conductor assembly of the present invention may be useful for augmenting traditional therapies such as antitachycardia pacing by altering the excitable gap through neural stimulation, thus improving the probability of pace termination of arrhythmias. Analogously, the passive conductor assembly and method for use thereof for neural stimulation may be beneficial for lowering the energy requirements for electrical termination of atrial or ventricular fibrillation. Neural stimulation can slow or even halt impulse propagation from the atria to the ventricles. Thus, the passive conductor assembly of the present invention should allow for control of the ventricular response to premature atrial contractions by slowing or stopping impulse propagation at the atrial-ventricular node. By causing transient heart block through neural stimulation, supra-ventricular arrhythmias such as Wolf-Parkinson-White Syndrome, atrial-ventricular nodal re-entrant tachycardia, atrial fibrillation or atrial flutter with rapid ventricular response and other arrhythmias may be successfully prevented, terminated, or controlled.

The utility of the compositions and methods according to the present invention are shown below in the Example section.

EXAMPLES

An example of the possible use of the passive conductor of the present invention is illustrated in FIG. 1. FIG. 1 illustrates the distribution of potentials generated with electrodes in the right ventricular cavity and on the skin of the left lower thorax. Even though the potential did change rapidly with distance in the lateral-apical left ventricle in the region marked A, signifying the potential gradient as low, the potential in this region for a 500V defibrillation shock was 83V more than the value on the epicardium overlying the electrode in the right ventricle in the region marked B [-48V-)-131V)]. If a wire was attached to the epicardium at these spots, current should flow through the wire and the potential gradient should be increased in the lateral-apical left ventricle. This should allow stimulation of the tissue in the lateral-apical left ventricle region with a much weaker stimulus than required in the absence of the wire.

For example, in the preferred embodiment of the invention an electric wire 100 has one end 102 both electrically and mechanically attached to a preselected region 104 of the heart, e.g. by suturing. A second end 106 of the wire 100 is both electrically and mechanically connected to a different region 108 of the heart, also preferably by suturing. Since the heart regions 104 and 108 of the heart attain different electric potentials during cardiac contraction, current flows through the wire thus achieving passive stimulation of the myocardium.

The wire 100 is electrically insulated in any conventional fashion between its ends 102 and 106. However, one or more points of the wire 100 between its ends may be electrically connected to the heart to provide passive stimulation during cardiac contraction.

As another example, the area near the pulmonary veins appears to frequently play a role in the induction and/or maintenance of atrial fibrillation. This is also the region in which the effect of the shock is weakest for electrodes in the right atrium and the distal coronary sinus as shown by Cooper et al. (Herzschr Elektrophys, 1998; 9:1–7). It should be possible to run a conductor to this region by way of the transverse sinus in the pericardial space. Such an electrode location should be beneficial for pacing to prevent atrial fibrillation, for giving a small pacing or shocking stimulus or stimuli just as atrial fibrillation begins, or for giving a defibrillation shock to halt atrial fibrillation once it is established.

Other descriptive and exemplary materials are provided in Appendix A herewith.

In view of the teaching presented herein, other modifications and variations of the present inventions will be readily apparent to those of skill in the art. The foregoing drawings, discussion, and description are illustrative of some embodiments of the present invention, but are not meant to be limitations on the practice thereof. It is the following claims, including all equivalents, which define the scope of the invention.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

What is claimed:

1. A method of electrically stimulating selected regions of a subject's heart, the subject having an implanted stimulus generator, the generator having an intracavitarily disposed electrode disposed in the subject, said method comprising the steps of:

inserting into the subject at least a first conductor having at least a first electrical contact and a second electrical contact thereon, the first conductor being electrically and mechanically separated from the implanted stimulus generator;

contacting a portion of the heart to be stimulated with the first electrical contact of the first conductor;

positioning the second electrical contact of the at least a first conductor in contact with myocardial tissue such that an electrical stimulus delivered by the implanted stimulus generator creates an electrical potential difference between the first electrical contact and the second electrical contact of the at least a first conductor;

generating a stimulus from the implanted stimulus generator; and discharging the electrical stimulus from the intracavitarily disposed electrode wherein the stimulus is conducted through the myocardial tissue and through the at least a first electrical conductor and is transferred to the portion of the heart contacting the first electrical contact of the at least a first conductor, whereby the stimulus is sufficient to stimulate selected regions of the heart.

2. A method according to claim 1, wherein said inserting step further comprises surgically implanting the at least a first conductor.

3. A method according to claim 2, wherein said surgically implanting step is further defined as thorascopically implanting the at least a first conductor.

4. A method according to claim 1, wherein the implanted stimulus generator is selected from the group consisting of a pacemaker and a defibrillator.

5. A method according to claim 1, wherein the conductor comprises an insulator disposed about at least a portion of the at least a first conductor.

6. A method according to claim 1, wherein the at least a first conductor comprises a metallic wire.

7. A method according to claim 1, wherein the at least a first conductor comprises a metallic strip.

8. A method according to claim 1, wherein the at least a first conductor comprises a ribbon of conductive material.

9. A method according to claim 1, wherein the at least a first conductor includes at least one electrical component disposed in electrical communication therewith.

10. A method according to claim 9, wherein the electrical component comprises a diode.

11. A method according to claim 9, wherein the electrical component comprises a device capable of storing energy.

12. A method according to claim 11, wherein the electrical component comprises a capacitor.

13. A method according to claim 9, wherein the electrical device comprises a resistor.

14. A method according to claim 9, wherein the electrical component comprises a microprocessor.

15. A method of neurally stimulating the heart of a subject, said method comprising the steps of:

disposing a conductor having at least two electrically conductive contacts adjacent to a portion of a heart in close proximity to an intracavitarily disposed electrode of an implanted stimulus generator, said conductor electrically and mechanically separated from said implanted stimulus generator;

contacting a portion of the heart with the at least two electrically conductive contacts of the conductor;

positioning the at least two electrically conductive contacts of the conductor in contact with myocardial tissue such that an electrical stimulus delivered by the implanted stimulus generator creates an electrical potential difference at each of the at least two electrically conductive contacts of the conductor inducing the flow of current therethrough; and generating an electrical stimulus from the implanted stimulus generator and discharging the electrical stimulus from the intracavitarily disposed electrode wherein the stimulus is conducted through the myocardial tissue and through at least one of the at least two electrically conductive contacts and is conducted to the regions of the heart contacting another of the at least two electrically conductive contacts of the conductor; and selectively stimulating neural tissue of the heart.

16. A method according to claim 15, wherein said inserting step further comprises surgically implanting the conductor.

17. A method according to claim 16, wherein said surgically implanting step is further defined as thorascopically implanting the conductor.

18. A method according to claim 15, wherein the implantable stimulus generator is selected from the group consisting of a pacemaker and a defibrillator.

19. A method according to claim 15, wherein the conductor comprises an insulator disposed about at least a portion of the conductor.

20. A method according to claim 15, wherein the conductor comprises a metallic wire.

21. A method according to claim 15, wherein the conductor comprises a metallic strip.

22. A method according to claim 15, wherein the conductor comprises a ribbon of conductive material.

23. A method according to claim 15, wherein the conductor includes at least one electrical component disposed in electrical communication therewith.

24. A method according to claim 23, wherein the at least one electrical component comprises a diode.

25. A method according to claim 23, wherein the at least one electrical component comprises a device capable of storing energy.

26. A method according to claim 25, wherein the at least one electrical component comprises a capacitor.

27. A method according to claim 23, wherein the at least one electrical device comprises a resistor.

28. A method according to claim 15, wherein the at least one electrical component comprises a microprocessor.

29. A method according to claim 15, wherein said selectively stimulating step further includes modifying the electrical stimulus prior to contacting the heart whereby the stimulus substantially only stimulates neural tissue.

* * * * *